(12) United States Patent
Hagen et al.

(10) Patent No.: US 7,692,038 B2
(45) Date of Patent: Apr. 6, 2010

(54) CRYSTALLINE FORMS

(75) Inventors: Eric Hagen, Lafayette, IN (US); Jason A. Hanko, West Lafayette, IN (US); Stuart Dimock, Lake Forest, CA (US)

(73) Assignee: Pfizer, Inc., New York, NY (US)

( * ) Notice: Subject to any disclaimer, the term of this patent is extended or adjusted under 35 U.S.C. 154(b) by 217 days.

(21) Appl. No.: 11/951,801

(22) Filed: Dec. 6, 2007

(65) Prior Publication Data

US 2008/0249031 A1    Oct. 9, 2008

Related U.S. Application Data

(60) Provisional application No. 60/868,748, filed on Dec. 6, 2006.

(51) Int. Cl.
    *C07C 229/00*    (2006.01)
(52) U.S. Cl. .......................... 562/448; 514/19
(58) Field of Classification Search ................ None
    See application file for complete search history.

(56) References Cited

U.S. PATENT DOCUMENTS 6,544,951 B2 *  4/2003  Karanewsky et al. .......... 514/19
2002/0042376 A1  4/2002  Karanewski et al.

FOREIGN PATENT DOCUMENTS

WO    WO-A-00/01666    1/2000

OTHER PUBLICATIONS

Linton et al, J. Med. Chem., vol. 48, No. 22, pp. 6779-6782 (2005).
Linton et al, J. Med. Chem., vol. 48, No. 22 pp. 1-23 (2005).

* cited by examiner

*Primary Examiner*—Daniel M Sullivan
*Assistant Examiner*—Sudhakar Katakam
(74) *Attorney, Agent, or Firm*—Pfizer, Inc.; Julie M. Lappin

(57) ABSTRACT

The present invention relates to crystalline forms of (3S)-3-[N—(N'-(2-tert-butylphenyl)oxamyl)alaninyl]amino-5-(2', 3',5',6'-tetrafluorophenoxy)-4-oxopentanoic acid (see formula I). The invention further relates to pharmaceutical compositions comprising such crystalline forms and to the use of said pharmaceutical compositions and said crystalline forms in the treatment of various conditions, particularly in the treatment of liver fibrosis.

(I)

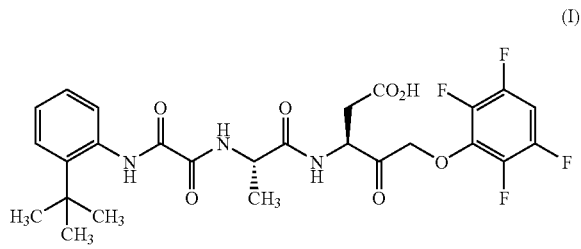

6 Claims, 10 Drawing Sheets

Figure 1 – DSC thermogram for Form I
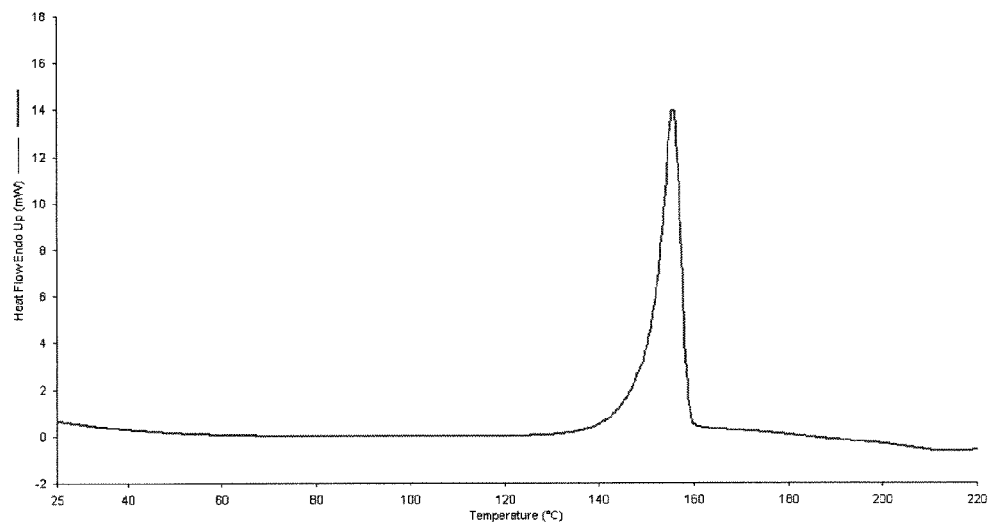
Figure 2 – PXRD pattern for Form I
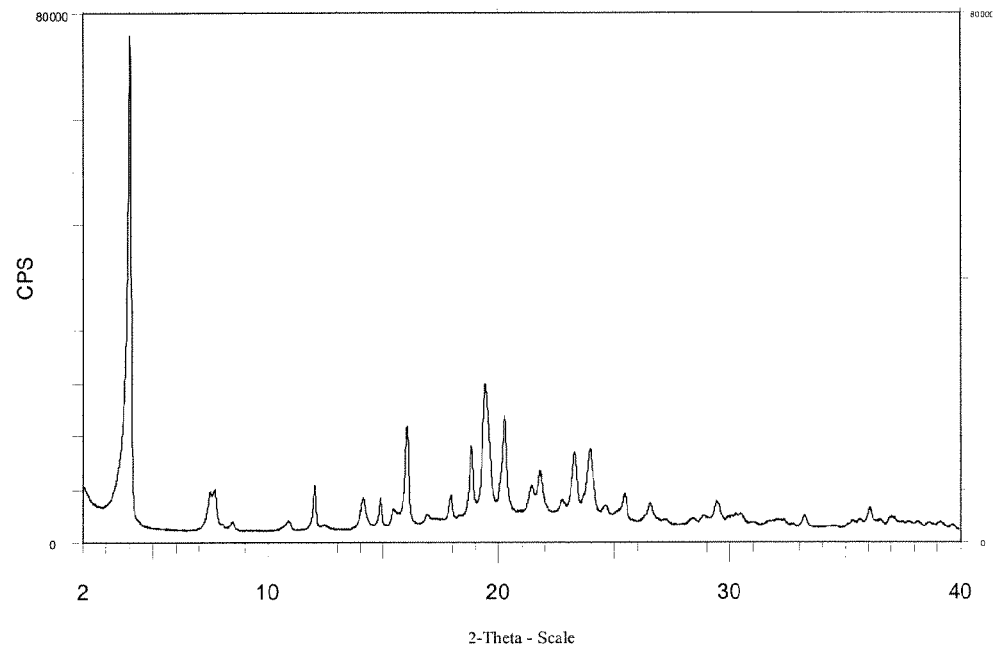

Figure 3 – Solid state $^{13}$C NMR spectrum for Form I
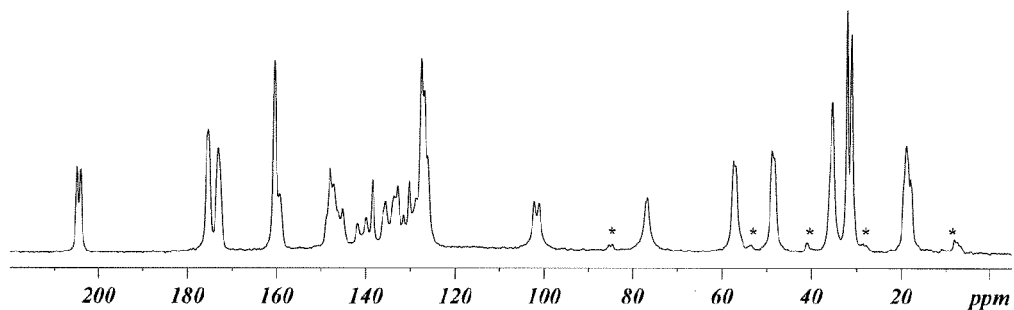
Figure 4 – Solid state $^{19}$F NMR spectrum for Form I
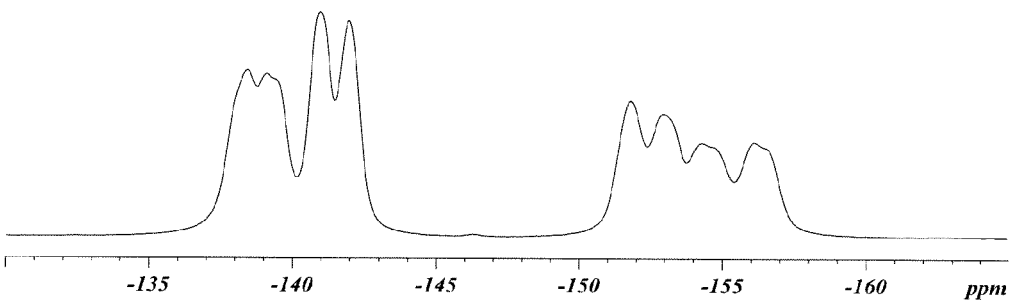

Figure 5 – FT-infra red spectrum for form I
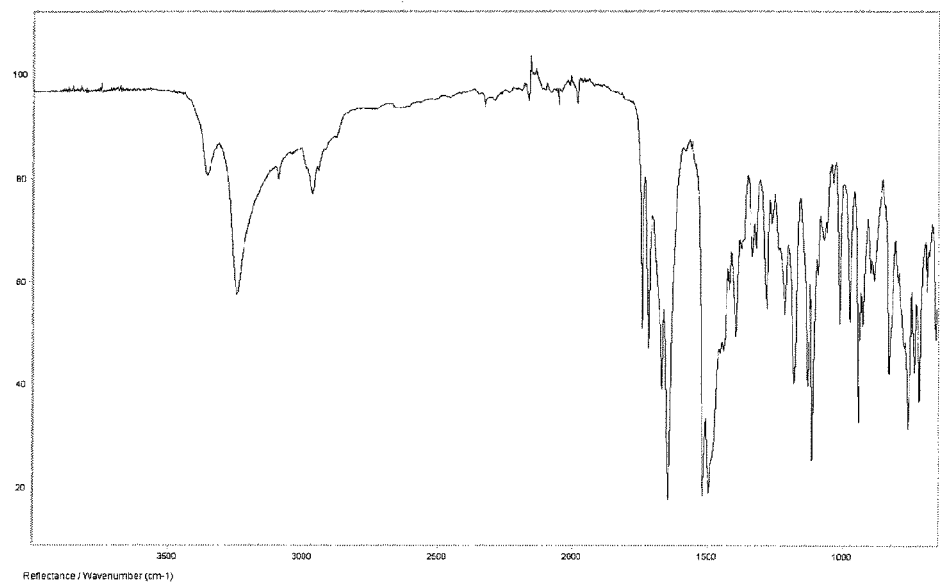
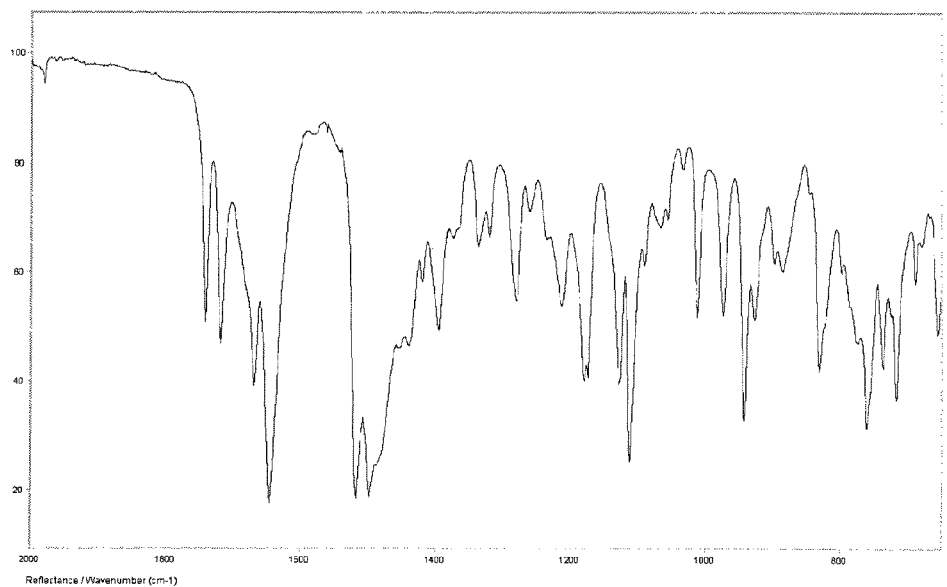

Figure 6 – FT-Raman spectrum for Form I
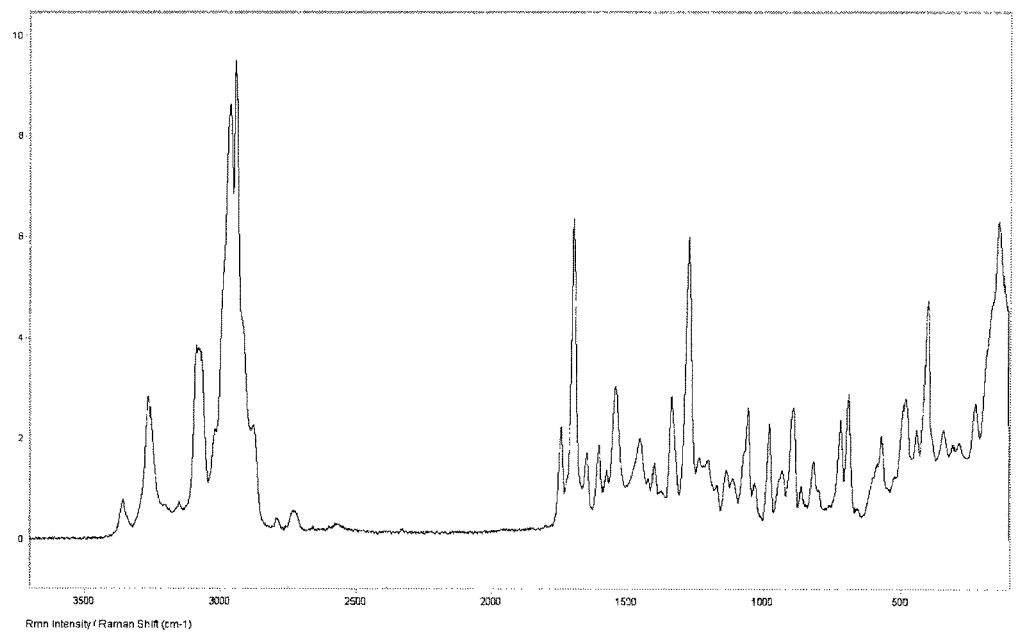
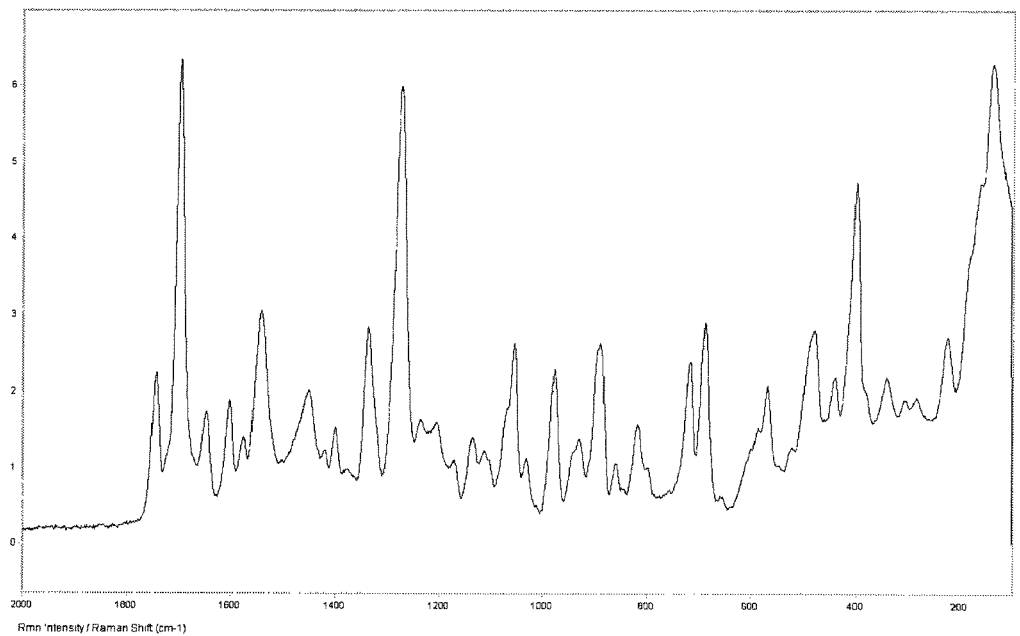

Figure 7 – DSC thermogram for Form II
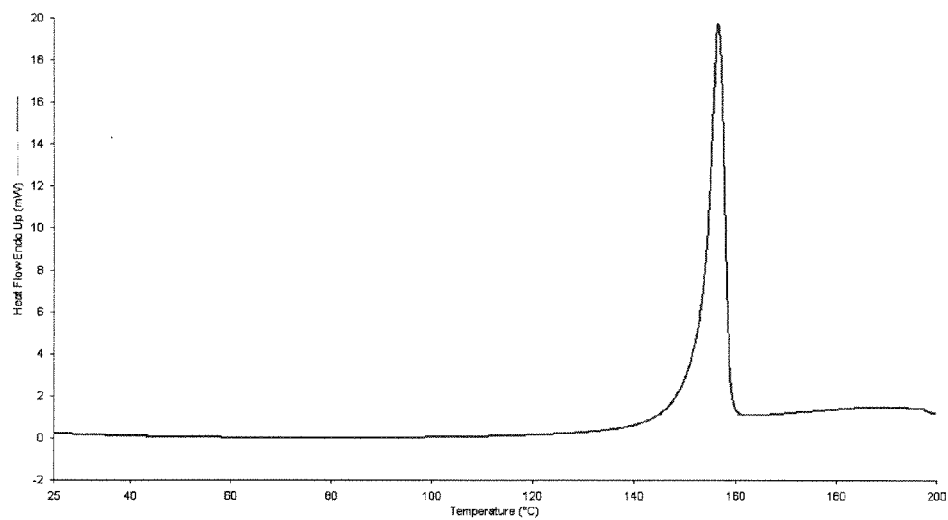
Figure 8 – PXRD pattern for Form II
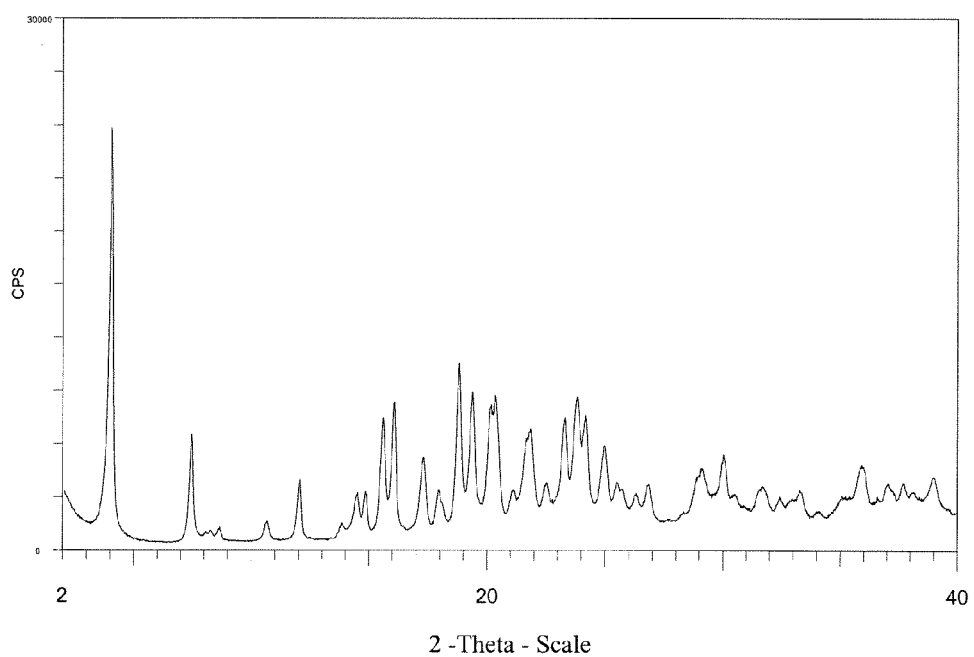

Figure 9 – Solid state $^{13}$C NMR spectrum for Form II
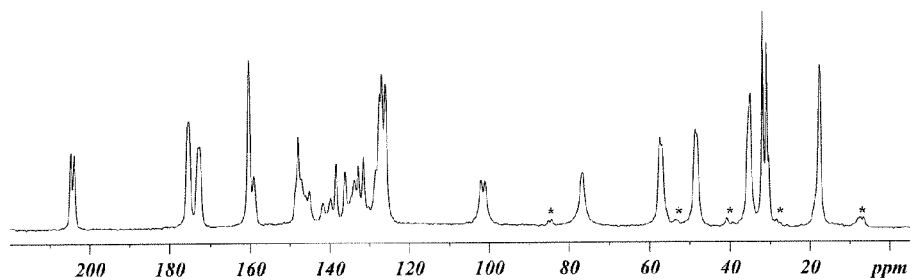
Figure 10 – Solid state $^{19}$F NMR spectrum for Form II
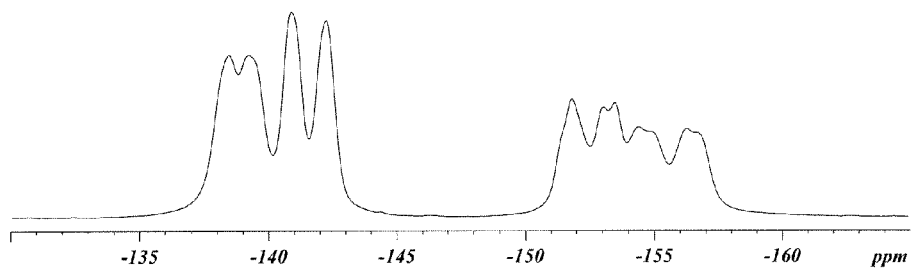

Figure 11 – FT-infra red spectrum for Form II
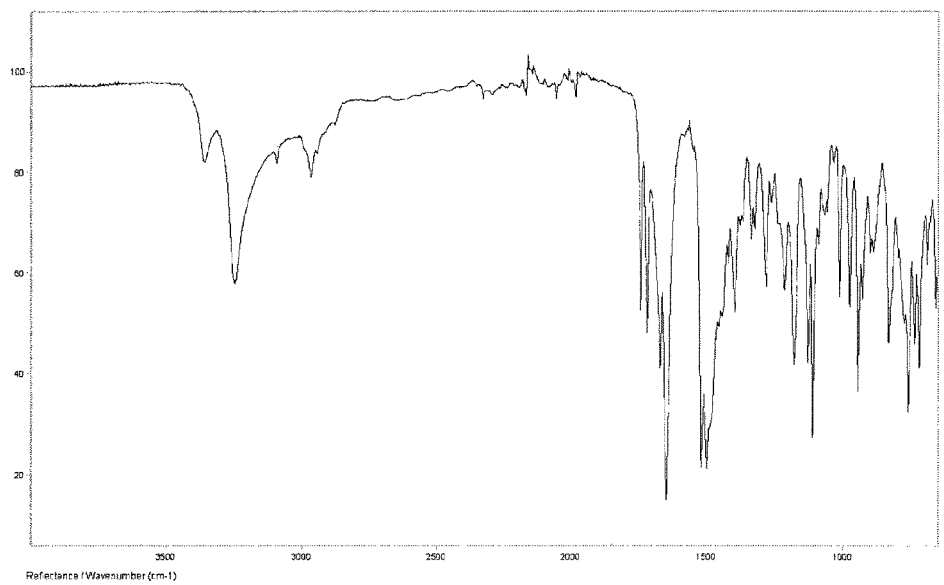
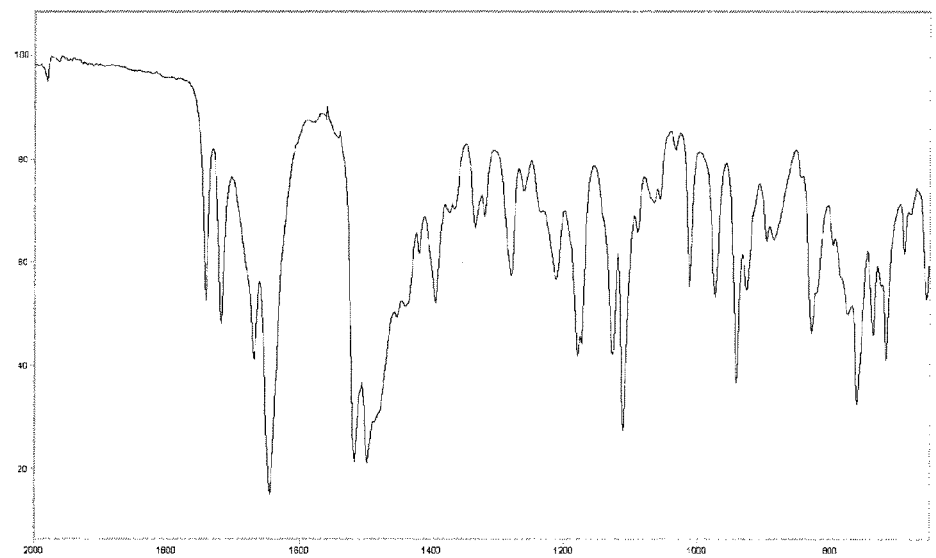

Figure 12 – FT-Raman spectrum for Form II
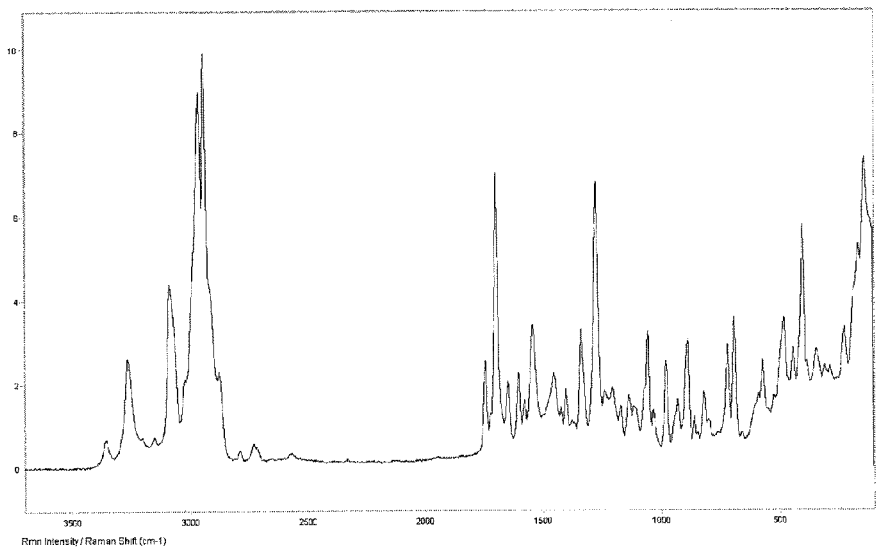
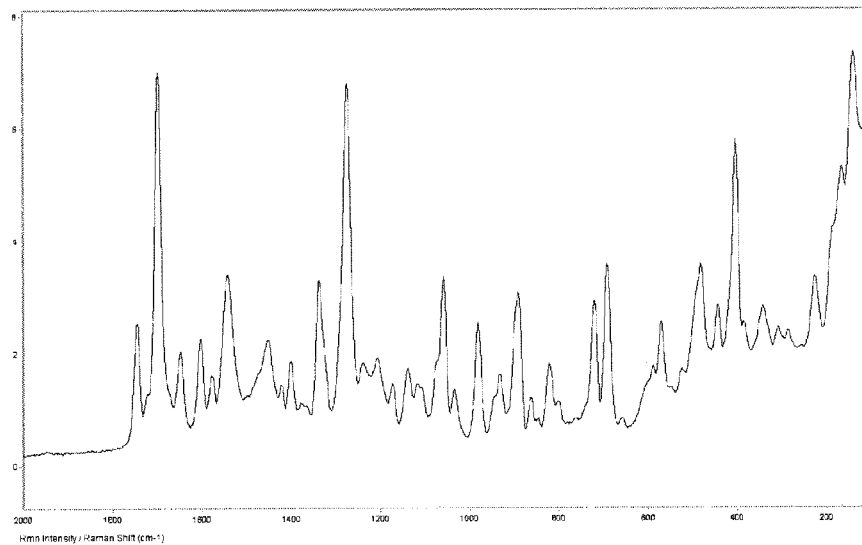

Figure 13 – DSC thermogram for Form III
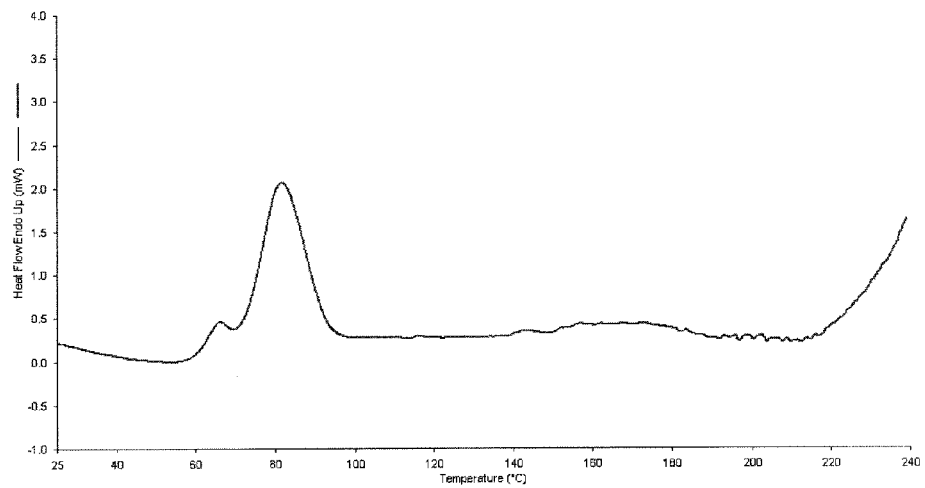
Figure 14 – PXRD pattern for Form III
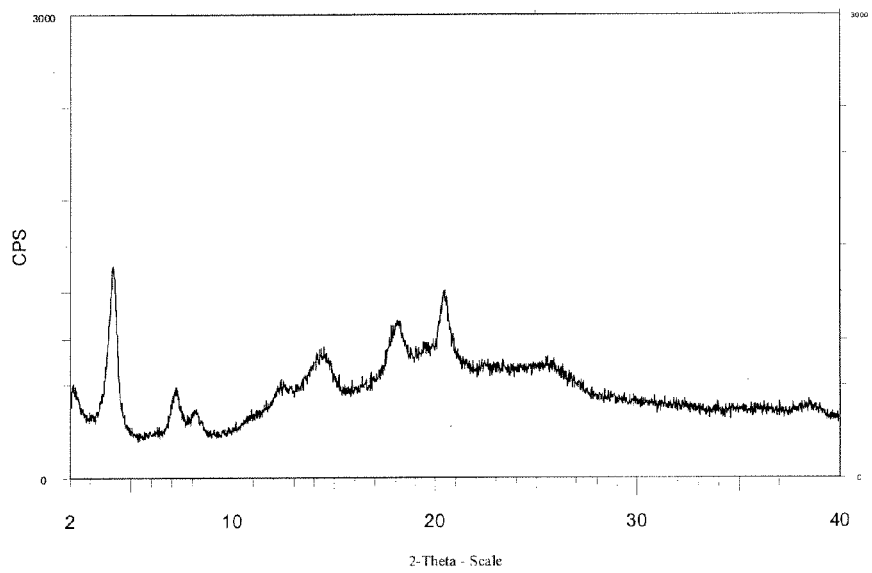

Figure 15 – Water sorption isotherm for Form I at 30°C
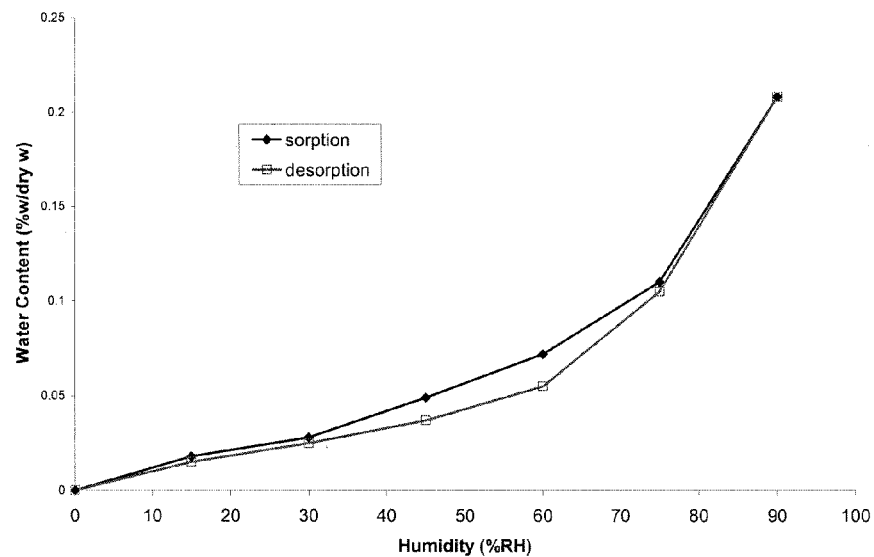
Figure 16 – Water sorption isotherm for Form II at 30°C
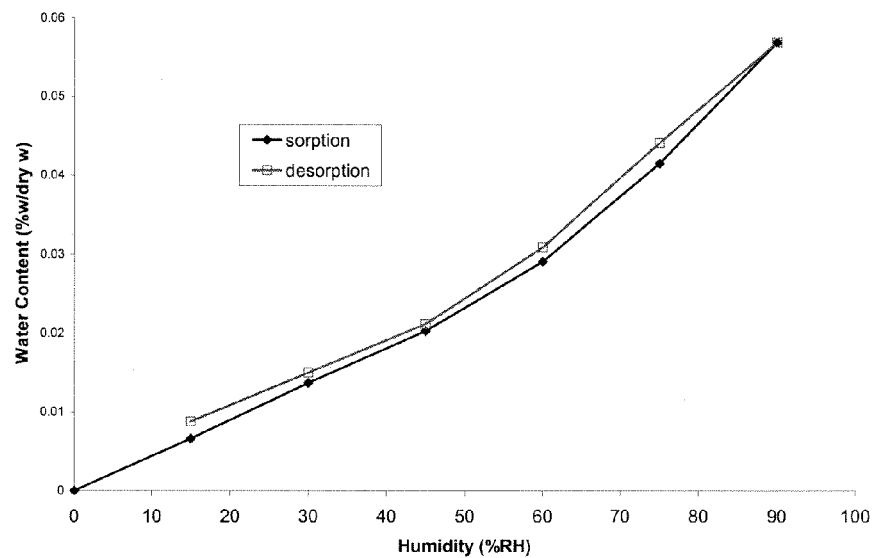

CRYSTALLINE FORMS

The present invention relates to crystalline forms of (3S)-3-[N—(N'-(2-tert-butylphenyl)oxamyl)alaninyl]amino-5-(2',3',5',6'-tetrafluorophenoxy)-4-oxopentanoic acid. The invention further relates to pharmaceutical compositions comprising such crystalline forms and to the use of said pharmaceutical compositions and said crystalline forms in the treatment of various conditions, particularly in the treatment of liver fibrosis.

The compound (3S)-3-[N—(N'-(2-tert-butylphenyl)oxamyl)alaninyl]amino-5-(2',3',5',6'-tetrafluorophenoxy)-4-oxopentanoic acid (also known as (3S)-3-[(2S)-2-({N[2-(tert-butyl)phenyl]carbomoyl}carbonylamino)propanoylamino]-4-oxo-5-(2,3,5,6-tetrafluorophenoxy)pentanoic acid) has the structure indicated by formula (I). This compound, and its preparation, are both disclosed in published international patent application WO-A-00/01666 (see Example 75). In the disclosed multi-step process, the compound is liberated by the deprotection of a corresponding tert-butyl ester using trifluoroacetic acid. Following silica chromatography, the compound is isolated as a colourless glass.

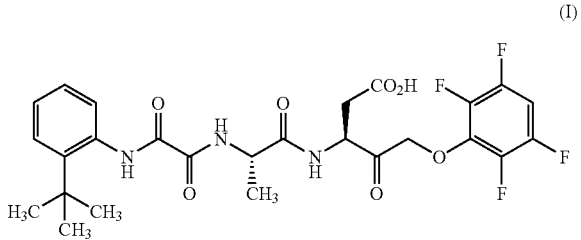

(I)

If a compound is to be developed as a drug, it is important to provide a form of that compound (commonly known as a drug substance) which can be reliably prepared and purified on a large scale and which does not degrade upon storage. A crystalline, and preferably high-melting, form of the compound is therefore desirable since high-melting point crystalline solids tend to be easy to purify by re-crystallisation and stable upon storage.

This invention provides, for the first time, a crystalline form of (3S)-3-[N—(N'-(2-tert-butylphenyl)oxamyl)alaninyl]amino-5-(2',3',5',6'-tetrafluorophenoxy)-4-oxopentanoic acid. Several specific polymorphs are described, along with processes by which they may be prepared.

The invention further provides: a pharmaceutical composition comprising a crystalline form of a compound of formula (I) and a pharmaceutically acceptable excipient; a crystalline form of a compound of formula (I) for use as a medicament; a crystalline form of a compound of formula (I) for use in the treatment of liver fibrosis; the use of a crystalline form of a compound of formula (I) for the manufacture of a medicament for the treatment of liver fibrosis; a method of treating liver fibrosis in a mammal comprising administering an effective amount of a crystalline form of a compound of formula (I) to a mammal in need of such treatment; and a combination of a crystalline form of a compound of formula (I) and a further pharmacologically active compound.

In a preferred aspect, the invention provides several specific polymorphic forms of a compound of formula (I). Each of these polymorphic forms has a unique three-dimensional crystalline configuration and can be characterised by, inter alia, the way the crystal lattice diffracts electromagnetic radiation (e.g. powder X-ray diffraction, infra-red spectroscopy, raman spectroscopy), its melting characteristics (e.g. differential scanning calorimetry) and solid state NMR analysis. For convenience, each of these polymorphic forms has been allocated a roman numeral, though these descriptors have no inherent technical significance.

BRIEF DESCRIPTION OF THE DRAWINGS

FIG. 1 shows a differential scanning calorimetry (DSC) thermogram for Form I.
FIG. 2 shows a powder X-ray diffraction (PXRD) pattern for Form I.
FIG. 3 shows a solid state $^{13}C$ NMR spectrum for Form I.
FIG. 4 shows a solid state $^{19}F$ NMR spectrum for Form I.
FIG. 5 shows a Fourier transform (FT)-infra red spectrum for Form I.
FIG. 6 shows a FT-Raman spectrum for Form I.
FIG. 7 shows a DSC thermogram for Form II.
FIG. 8 shows a PXRD pattern for Form II.
FIG. 9 shows a solid state $^{13}C$ NMR spectrum for Form II.
FIG. 10 shows a solid state $^{19}F$ NMR spectrum for Form II.
FIG. 11 shows a FT-infra red spectrum for Form II.
FIG. 12 shows a FT-Raman spectrum for Form II.
FIG. 13 shows a DSC thermogram for Form III.
FIG. 14 shows a PXRD pattern for Form III.
FIG. 15 shows a water sorption isotherm for Form I at 30° C.
FIG. 16 shows a water sorption isotherm for Form II at 30° C.

Form I shows a sharp, endothermic peak at 156° C. (±2° C.) when analysed by differential scanning calorimetry (DSC) due to melting. The observed DSC thermogram is reproduced as FIG. 1. Form I gives unique peaks at 7.7, 14.1, 21.4, 26.6 and 29.4 degrees two theta (±0.1 degrees) when analysed by powder X-ray diffraction (PXRD). The observed PXRD pattern is reproduced as FIG. 2 and the full peak listing is provided in Table 1 below.

TABLE 1

PXRD data for Form I

| Angle 2-Theta (degrees) | Relative Intensity (%) |
| --- | --- |
| 4.0 | 100.0 |
| 7.4 | 10.1 |
| 7.7 | 10.1 |
| 11.9 | 9.3 |
| 12.0 | 11.0 |
| 14.1 | 8.6 |
| 14.9 | 8.6 |
| 15.4 | 6.4 |
| 16.0 | 22.7 |
| 17.9 | 8.9 |
| 18.8 | 19.0 |
| 19.4 | 31.0 |
| 19.5 | 25.0 |
| 20.3 | 24.8 |
| 21.4 | 10.9 |
| 21.8 | 13.9 |
| 22.8 | 8.2 |
| 23.3 | 17.6 |
| 24.0 | 18.1 |
| 24.1 | 15.3 |
| 24.6 | 7.0 |
| 25.5 | 9.3 |
| 26.6 | 7.6 |
| 29.4 | 8.0 |
| 29.6 | 6.7 |
| 36.1 | 6.6 |

Form I displays unique chemical shifts at 135.6, 127.5 and 18.8 ppm when analysed by solid phase $^{13}$C NMR using an external sample of solid phase adamantine at 29.5 ppm as the reference. The observed $^{13}$C NMR spectrum is reproduced as FIG. 3 (peaks marked with an asterisk are spinning side bands) and the full peak listing is provided in Table 2 below. The intensity values are a measure of peak height and these can vary according to the experimental parameters set during the data acquisition and the thermal history of the sample—they are not therefore intended to have any quantitative significance.

TABLE 2

$^{13}$C NMR data for Form I

| $^{13}$C chemical shift (ppm) | Intensity |
|---|---|
| 204.9 | 4.1 |
| 204.1 | 3.9 |
| 175.3 | 5.9 |
| 173.1 | 5.0 |
| 160.4 | 9.4 |
| 159.3 | 2.7 |
| 148.0 | 4.0 |
| 147.2 | 3.2 |
| 146.2 | 1.8 |
| 145.2 | 1.9 |
| 141.8 | 1.2 |
| 139.9 | 1.5 |
| 138.5 | 3.4 |
| 135.6 | 2.3 |
| 133.7 | 2.6 |
| 132.9 | 3.1 |
| 131.6 | 1.6 |
| 130.4 | 3.4 |
| 128.8 | 2.5 |
| 127.5 | 9.5 |
| 127.0 | 7.9 |
| 126.2 | 4.6 |
| 102.2 | 2.3 |
| 101.2 | 2.2 |
| 76.7 | 2.5 |
| 57.4 | 4.4 |
| 57.0 | 4.1 |
| 48.8 | 4.9 |
| 35.2 | 7.3 |
| 32.0 | 12.0 |
| 31.0 | 10.7 |
| 18.8 | 5.1 |
| 17.9 | 3.5 |

Form I displays a unique chemical shift at −141.9 ppm when analysed by solid phase $^{19}$F NMR using an external sample of trifluoroacetic acid (50% volume/volume in water) at −76.54 ppm as a reference. The observed $^{19}$F NMR spectrum is reproduced as FIG. 4 (only the centreband portion of the spectrum is shown). The full peak listing is −138.4, −139.1, −139.4 (shoulder), −140.9, −141.9, −151.8, −152.9, −154.2, −154.7 (shoulder), −156.1 and −156.5 (shoulder) ppm.

Form I displays characteristic peaks at wavenumber 3354 (weak), 3243 (medium), 3089 (weak), 2962 (weak), 1741 (medium), 1718 (medium), 1668 (medium), 1646 (strong), 1517 (strong), 1497 (strong), 1419 (weak), 1394 (medium), 1335 (weak), 1320 (weak), 1280 (medium), 1260 (weak), 1212 (medium), 1179 (medium), 1174 (weak), 1127 (medium), 1111 (strong), 1089 (weak), 1032 (weak), 1011 (medium), 973 (medium), 941 (strong), 926 (weak), 897 (weak), 885 (medium), 829 (medium), 759 (strong), 735 (medium), 715 (medium), 687 (weak) and 653 (medium) cm$^{-1}$ when analysed by FT-infra red spectroscopy (±2 cm$^{-1}$ except for peak at 3243 where the error limit can be considerably larger). Intensity assignments (weak, medium, strong) are relative to the major peak in the spectrum. The spectrum is reproduced as FIG. 5.

Form I displays characteristic peaks at wavenumber 3356 (weak), 3262 (medium), 3086 (medium), 2959 (strong), 2939 (strong), 1742 (medium), 1695 (medium strong), 1647 (weak), 1601 (weak), 1541 (medium), 1451 (weak), 1399 (weak), 1336 (medium), 1271 (medium strong), 1135 (weak), 1054 (medium), 1031 (weak), 977 (medium), 930 (weak), 888 (medium), 859 (weak), 817 (weak), 716 (medium), 688 (medium), 568 (medium), 479 (medium), 439 (weak), 398 (medium), 340 (weak), 223 (weak) cm$^{-1}$ when analysed by FT-Raman spectroscopy (±2 cm$^{-1}$ except for peaks at 2959, 1541, 1451, 1271, 1135, 1054, 1031, 977, 930, 888, 859, 716, 688, 568, 479, 439, 398 and 223 where the error limit is (±5 cm$^{-1}$). Intensity assignments (weak, medium, medium strong, strong) are relative to the major peak in the spectrum. The spectrum is reproduced as FIG. 6.

Form II shows a sharp endothermic peak at 157° C. (±2° C.) when analysed by DSC (see FIG. 7). Form II displays unique diffraction peaks at 14.5, 17.3, 22.5, 25.0 and 26.8 degrees two theta (±0.1 degrees) when analysed by PXRD (see FIG. 8). A peak listing is provided below in Table 3.

TABLE 3

PXRD data for Form II

| Angle 2-Theta (degrees) | Relative Intensity (%) |
|---|---|
| 4.0 | 100.0 |
| 7.4 | 27.2 |
| 12.0 | 16.6 |
| 14.5 | 12.9 |
| 14.8 | 13.7 |
| 15.6 | 31.2 |
| 16.1 | 35.0 |
| 17.3 | 21.9 |
| 17.9 | 14.1 |
| 18.1 | 11.3 |
| 18.8 | 44.1 |
| 19.4 | 37.4 |
| 20.2 | 33.8 |
| 20.4 | 36.5 |
| 21.1 | 14.2 |
| 21.7 | 27.4 |
| 21.8 | 28.5 |
| 22.5 | 15.9 |
| 23.3 | 31.2 |
| 23.8 | 36.2 |
| 24.2 | 32.1 |
| 25.0 | 24.6 |
| 25.5 | 16.0 |
| 25.7 | 14.3 |
| 26.3 | 13.0 |
| 26.8 | 15.6 |
| 28.9 | 17.3 |
| 29.1 | 19.3 |
| 30.0 | 22.5 |
| 30.5 | 13.2 |
| 30.9 | 10.7 |
| 31.7 | 15.0 |
| 32.5 | 12.6 |
| 33.0 | 12.2 |
| 33.3 | 14.1 |
| 35.2 | 12.2 |
| 36.0 | 20.1 |
| 36.6 | 12.6 |
| 37.1 | 15.7 |
| 37.3 | 14.1 |
| 37.7 | 15.9 |

TABLE 3-continued

PXRD data for Form II

| Angle 2-Theta (degrees) | Relative Intensity (%) |
|---|---|
| 38.1 | 13.8 |
| 39.0 | 17.2 |

Form II displays unique chemical shifts at 136.2, 131.6, 126.1, 30.4 and 17.7 ppm when analysed by solid phase $^{13}$C NMR using an external sample of solid phase adamantine at 29.5 ppm as the reference. The observed $^{13}$C NMR spectrum is reproduced as FIG. 9 (peaks marked with an asterisk are spinning side bands) and the full peak listing is provided in Table 4 below. The intensity values are a measure of peak height and these can vary according to the experimental parameters set during the data acquisition and the thermal history of the sample—they are not therefore intended to have any quantitative significance.

TABLE 4

$^{13}$C NMR data for Form II

| $^{13}$C chemical shift (ppm) | Intensity |
|---|---|
| 204.8 | 4.1 |
| 204.0 | 4.0 |
| 175.5 | 5.8 |
| 175.3 | 5.9 |
| 173.0 | 4.4 |
| 172.7 | 4.4 |
| 160.4 | 9.4 |
| 159.1 | 2.7 |
| 148.0 | 5.0 |
| 147.1 | 2.6 |
| 146.2 | 1.6 |
| 145.1 | 1.9 |
| 141.8 | 1.2 |
| 139.9 | 1.5 |
| 138.5 | 3.4 |
| 136.2 | 3.0 |
| 133.9 | 2.5 |
| 132.9 | 3.3 |
| 131.6 | 3.8 |
| 130.4 | 1.0 |
| 128.5 | 3.1 |
| 127.5 | 7.4 |
| 127.0 | 8.5 |
| 126.1 | 8.0 |
| 102.1 | 2.5 |
| 101.1 | 2.4 |
| 76.6 | 2.9 |
| 57.5 | 4.8 |
| 56.9 | 4.4 |
| 48.7 | 5.3 |
| 35.1 | 7.4 |
| 32.0 | 12.0 |
| 31.0 | 10.3 |
| 30.4 | 3.8 |
| 17.7 | 9.0 |

Form II displays unique chemical shifts at −142.2 and −153.4 ppm when analysed by solid phase $^{19}$F NMR using an external sample of trifluoroacetic acid (50% volume/volume in water) at −76.54 ppm as a reference. The observed $^{19}$F NMR spectrum is reproduced as FIG. 10 (only the centreband portion of the spectrum is shown). The full peak listing is −138.4, −139.2, −140.9, −142.2, −151.8, −153.0, −153.4, −154.4, −154.9 (shoulder), −156.2 and −156.7 (shoulder) ppm.

Form II displays characteristic peaks at wavenumber 3355 (weak), 3244 (medium), 3089 (weak), 2962 (weak), 1741 (medium), 1719 (medium), 1669 (medium), 1646 (strong), 1517 (strong), 1498 (strong), 1394 (medium), 1334 (weak), 1320 (weak), 1279 (medium), 1260 (weak), 1211 (medium), 1180 (medium), 1174 (weak), 1127 (medium), 1112 (strong), 1089 (weak), 1031 (weak), 1011 (medium), 973 (medium), 941 (strong), 926 (weak), 896 (weak), 885 (medium), 829 (medium), 759 (strong), 734 (medium), 715 (medium), 687 (weak) and 653 (medium) cm$^{-1}$ when analysed by FT-infra red spectroscopy (±2 cm$^{-1}$ except for peak at 3244 where the error limit can be considerably larger). Intensity assignments (weak, medium, strong) are relative to the major peak in the spectrum. The spectrum is reproduced as FIG. 11.

Form II displays characteristic peaks at wavenumber 3356 (weak), 3262 (medium), 3087 (medium), 2960 (strong), 2938 (strong), 1743 (medium), 1696 (medium strong), 1647 (weak), 1602 (weak), 1541 (medium), 1451 (weak), 1400 (weak), 1336 (medium), 1272 (medium strong), 1136 (weak), 1056 (medium), 1032 (weak), 979 (medium), 930 (weak), 888 (medium), 861 (weak), 818 (medium), 718 (medium), 689 (medium), 570 (medium), 480 (medium), 441 (weak), 400 (medium), 340 (weak), 223 (weak) cm$^{-1}$ when analysed by FT-Raman spectroscopy (±2 cm$^{-1}$ except for peaks at 2960, 1541, 1451, 1272, 1136, 1056, 1032, 979, 930, 888, 861, 718, 689, 570, 480, 441, 400 and 223 where the error limit is ±5 cm$^{-1}$). Intensity assignments (weak, medium, medium strong, strong) are relative to the major peak in the spectrum. The spectrum is reproduced as FIG. 12.

Form III shows a broad endothermic peak at 82° C. (±2° C.), with a peak shoulder at 66° C. (±2° C.) when analysed by DSC (see FIG. 13). Form III displays a unique diffraction peak at 7.2 degrees two theta (±0.1 degrees) when analysed by PXRD (see FIG. 14). A peak listing is provided below in Table 5.

TABLE 5

PXRD data for Form III

| Angle 2-Theta (degrees) | Relative Intensity (%) |
|---|---|
| 4.0 | 100.0 |
| 7.2 | 42.5 |
| 8.1 | 33.4 |
| 8.4 | 28.8 |
| 12.4 | 47.0 |
| 14.4 | 60.8 |
| 16.5 | 45.0 |
| 18.0 | 75.4 |
| 19.6 | 64.2 |
| 20.4 | 88.0 |
| 25.6 | 56.4 |
| 38.5 | 36.2 |

In the experiments conducted in order to accumulate the DSC data described above, the samples of Forms I and III were heated from 25 to 240° C. and the sample of Form II was heated from 25 to 200° C. at 20° C. per minute using a Perkin Elmer Pyris Diamond DSC in 50 microlitre aluminium pans with holes and lids, with a nitrogen purge gas.

In the experiments conducted in order to accumulate the PXRD data described above, the powder X-ray diffraction pattern for Form I was determined using a Bruker-AXS Ltd D8 Advance powder X-ray diffractometer fitted with a capillary stage, a theta-theta goniometer, a copper K-alpha$_1$ primary monochromator and a Braun position sensitive detector. The sample was mounted in a 1.0 mm quartz capillary. The sample was rotated whilst being irradiated with copper K-alpha$_1$ X-rays (wavelength=1.5406 Angstroms) with the X-ray tube operated at 40 kV/40 mA. The analyses were performed with the goniometer running in a continuous mode set for a 6 second count per 0.007° step over a two theta range of 2° to 40°.

The powder X-ray diffraction pattern for Form II was determined using a Bruker-AXS Ltd D4 powder X-ray diffractometer fitted with an automatic sample changer, a theta-theta goniometer, automatic beam divergence slit, and a PSD Vantec-1 detector. The sample was prepared for analysis by filling a cavity silicon wafer specimen mount. The specimen was rotated whilst being irradiated with copper K-alpha$_1$ X-rays (wavelength=1.5406 Angstroms) with the X-ray tube operated at 40 kV/30 mA. The analyses were performed with the goniometer running in continuous mode set for a 0.6 second count per 0.018° step over a two theta range of 2° to 40°.

The powder X-ray diffraction pattern for Form III was determined using a Bruker-AXS Ltd D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha$_1$ X-rays (wavelength=1.5406 Angstroms) with the X-ray tube operated at 40 kV/40 mA. The analyses were performed with the goniometer running in continuous mode set for a 0.2 second count per 0.018° step over a two theta range of 2° to 40°. The peaks obtained were aligned against a silicon reference standard.

As will be appreciated by the skilled person, the relative intensities of the various peaks within Tables 1, 3 and 5 may vary due to a number of factors such as for example orientation effects of crystals in the X-ray beam or the purity of the material being analysed or the degree of crystallinity of the sample. The peak positions may also shift for variations in sample height but the peak positions will remain substantially as defined in Tables 1, 3 and 5. The skilled person will also appreciate that measurements using a different wavelength will result in different shifts according to the Bragg equation ($n\lambda=2d \sin \theta$). Such further PXRD patterns generated by use of alternative wavelengths are alternative representations of the PXRD patterns of the crystalline materials of the present invention.

In order to accumulate the solid state NMR data described above, approximately 80 mg of each sample was tightly packed into a 4 mm ZrO$_2$ spinner. The spectra were collected at ambient conditions on a Bruker-Biospin 4 mm BL HFX CPMAS probe positioned into a wide-bore Bruker-Biospin Avance DSX 500 MHz NMR spectrometer. The samples were oriented at the magic angle and spun at 15.0 kHz. The fast spinning speed minimized the intensities of the spinning side bands. The number of scans was adjusted to obtain an adequate signal to noise ratio.

The $^{19}$F solid state spectra were collected using a proton decoupled magic angle spinning (MAS) experiment. The spectra were acquired with spectral width of 200 ppm. The proton decoupling field of approximately 80 kHz was applied and 64 scans were collected on each $^{19}$F MAS spectrum. The recycle delay was set to 400 seconds to ensure acquisition of quantitative spectra. The spectra were referenced using an external sample of trifluoroacetic acid (50% volume/volume in water), setting its resonance to −76.54 ppm.

The $^{13}$C solid state spectra were collected using a proton decoupled cross-polarization magic angle spinning experiment (CPMAS). The Hartman-Hahn contact time was set to 2 ms. The proton decoupling field of approximately 85 kHz was applied and 8192 scans were collected. The recycle delay was adjusted to 3 seconds. The spectrum was referenced using an external standard of crystalline adamantane, setting its upfield resonance to 29.5 ppm.

The FT-infra red spectra described above were acquired using a ThermoNicolet Avatar FTIR spectrometer equipped with a 'Golden Gate™' single reflection ATR accessory (diamond top plate and zinc selenide lenses) and DTGS KBr detector. The spectra were collected at 2 cm$^{-1}$ resolution with a co-addition of 256 scans. Happ-Genzel apodization was used. Because the FT-IR specta were recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$.

The FT-Raman spectra described above were collected using a ThermoNicolet 960 FT-Raman spectrometer equipped with a 1064 nm NdYAG laser and Germanium detector. The spectrum for Form I was collected using 460 mW laser power at the sample with 4112 co-added scans at 2 cm$^{-1}$ resolution. The spectrum for Form II was collected using 510 mW laser power at the sample with 8000 co-added scans at 2 cm$^{-1}$ resolution. Happ-Genzel apodization was used. Each sample was placed in a glass vial and exposed to the laser radiation. The data are presented as Raman intensity as a function of Raman shift. Experimental error, unless otherwise noted, was ±2 cm$^{-1}$.

The crystalline forms of the invention may be prepared by the processes described below. The skilled person will understand that the preparation of particular polymorphic forms of a compound can sometimes be problematic, and that small changes in reaction conditions can sometimes result in an unexpected product. In particular, the presence of seeds in the atmosphere under which the experiment is conducted can have a decisive outcome on the result. The processes described below, however, are generally reliable. The form II polymorph is the most thermodynamically stable at ambient temperature and its formation is encouraged by slow crystallisation. The form I polymorph is the more kinetically favoured product at ambient temperature and its formation is encouraged by rapid crystallisation techniques such as rapid cooling. Seeding with the desired product will obviously increase success in these preparations. Preparation of form I material is particularly encouraged by the use of a form I seed which contains a mixture of diastereomers due to epimerisation at the modified aspartate residue.

Preparation of a Mixture of Form I and Form II

A mixture of crystalline forms I and II can be prepared by crystallisation of amorphous (3S)-3-[N—(N'-(2-tert-butylphenyl)oxamyl)alaninyl]amino-5-(2',3', 5',6'-tetrafluorophenoxy)-4-oxopentanoic acid (or any other form of the compound) from a mixture of acetic acid and water. This process occasionally gives pure form I product.

For example, (3S)-3-[N—(N'-(2-tert-butylphenyl)oxamyl)alaninyl]amino-5-(2',3',5',6'-tetrafluorophenoxy)-4-oxopentanoic acid (15.033 g) was charged into a flask equipped with a magnetic stirrer bar. Acetic acid (200 ml) was added, with stirring, to give a solution to which activated carbon (1.512 g) was added. The resulting black suspension was stirred at ambient temperature for 10 minutes and filtered under vacuum, the solid residue being washed twice with acetic acid (2×40 ml). The combined filtrate was diluted with deionised water (155 ml) to give a turbid solution which became clear on warming to about 42° C. An additional portion of deionised water (225 ml) was added, restoring turbidity and the solution was allowed to cool slowly to ambient temperature with stirring, giving a white crystalline material (mixture of forms I and II).

Preparation of Pure Form II from a Mixture of Forms I and II Without Seeding

Pure form II may be prepared by slurrying a mixture of forms I and II in acetonitrile at room temperature until full conversion has taken place (typically a few days, e.g. 3 days). The product is then filtered off and dried (e.g. in a vacuum oven). The following procedures are illustrative.

A 40:60 mixture (by weight) of forms I and II was slurried in acetonitrile and left for three days. The solid product was then filtered and dried in a vacuum oven to give pure, crystalline form II. This material can be used as a seed, where necessary, in further experiments described below.

A slurry of (3S)-3-[N—(N'-(2-tert-Butylphenyl)oxamyl) alaninyl]amino-5-(2',3',5',6'-tetrafluorophenoxy)-4-oxopentanoic acid (1.5 g, approximately 40:60 Form I:Form II by weight) in acetonitrile (13 ml) was stirred for 3 days at room temperature (22° C.). The solid phase was separated by filtration and dried for 16 hours under vacuum (22° C. and 25 mbar) to give pure Form II as the product in 86% yield.

Pure form II can also be generated by slurrying a mixture of forms I and II at 4° C. for a period of days (e.g. for about 5 days) in a solvent selected from ethyl acetate, toluene, ethyl acetate/water, ethyl acetate/acetonitrile and isopropyl alcohol (IPA). Pure form II can also be prepared by slurrying a mixture of forms I and II at about 50° C. in dichloromethane or methyl ethyl ketone.

Preparation of Pure Form II from a Mixture of Forms I and II Using Seeding

A slurry of (3S)-3-[N—(N'-(2-tert-butylphenyl)oxamyl) alaninyl]amino-5-(2',3',5',6'-tetrafluorophenoxy)-4-oxopentanoic acid (40 g, approximately 90:10 Form I:Form II by weight) in a mixture of isopropyl alcohol and water (400 ml, 93:7 by volume) was prepared. The slurry was heated from 22° C. to 60° C. over 30 minutes and the resulting solution was held at 60° C. for a period of 30 minutes to allow equilibrium to be reached. Complete dissolution had occurred at this point. The solution was cooled to 25° C. over a period of 30 minutes and, once at 25° C., the supersaturated solution was seeded with crystals of Form II. The seed concentration used was 0.4 g or 1% w/w of initial feed concentration. The slurry was held at 25° C. for a period of 4 hours, cooled from 25° C. to 0° C. over a period of 4 hours and held at 0° C. for a period of 12 hours. The slurry was vacuum filtered and the solid product was dried in a vacuum oven at 50° C. for 60 hours. The product was isolated in a yield of 80% (32 g). PXRD analysis of both pre- and post-drying samples was consistent with Form II.

Preparation of Pure Form II from Form I Using Seeding

A slurry of (3S)-3-[N—(N'-(2-tert-butylphenyl)oxamyl) alaninyl]amino-5-(2',3',5',6'-tetrafluorophenoxy)-4-oxopentanoic acid (22.5 g, 100% Form I) in a mixture of isopropyl alcohol and water (300 ml, 93:7 by volume) was prepared in a flask equipped with a 3-blade retreat curve impeller, operating at 250 rpm. The slurry was heated from 25° C. to 50° C. over 30 minutes. The solution was held at 50° C. for a period of 30 minutes to allow equilibrium to be reached. It was ensured that complete dissolution had occurred at this point. The solution was cooled to 35° C. over a period of 30 minutes. Once at 35° C., the supersaturated solution was seeded with PF-3,491,390 Form II. The seed concentration used was 0.225 g or 1% w/w of initial feed concentration. The seed used in this experiment was micronised. The slurry was held at seed temperature i.e. 35° C. for a period of 3 hours. The slurry was cooled from 35° C. to −5° C. over a period of 24 hours. The slurry was held at −5° C. for a period of 18 hours. The slurry was vacuum filtered and dried in a vacuum oven at 50° C. to give 21.6 g of PF-3,491,390 (95%). PXRD analysis of both pre- and post-drying samples was consistent with Form II.

Preparation of Pure Form I from a Mixture of Form I and Form II

Pure form I may be prepared by dissolving a mixture of forms I and II in the minimum amount of a polar organic solvent (typically isopropylalcohol (IPA), tetrahydrofuran (THF) or acetic acid) at an elevated temperature (typically at about 50° C.) and allowing crystallisation to occur by cooling to a lower temperature (typically to about 4° C., overnight). A non-polar organic solvent such as n-heptane or trifluorotoluene (usually referred to as an anti-solvent) may be added in order to aid crystallisation. The following experiments are illustrative.

(3S)-3-[N—(N'-(2-tert-Butylphenyl)oxamyl)alaninyl] amino-5-(2',3',5',6'-tetrafluorophenoxy)-4-oxopentanoic acid (300 mg, approximately 40:60 Form I Form II) was dissolved in the minimum amount of isopropyl alcohol (4 ml) at 50° C. This solution was then cooled to 4° C. at 0.5° C./minute and stirred at 4° C. overnight to give pure Form I as the product.

(3S)-3-[N—(N'-(2-tert-Butylphenyl)oxamyl)alaninyl] amino-5-(2',3',5',6'-tetrafluorophenoxy)-4-oxopentanoic acid (200 mg, approximately 40:60 Form I:Form II) was dissolved in 0.3 ml of tetrahydrofuran at 50° C. n-Heptane (0.9 ml) was added as an anti-solvent to cause precipitation. The resulting slurry was cooled to 4° C. at 0.5° C./minute and stirred at 4° C. overnight to give pure Form I as the product.

(3S)-3-[N—(N'-(2-tert-Butylphenyl)oxamyl)alaninyl] amino-5-(2',3',5',6'-tetrafluorophenoxy)-4-oxopentanoic acid (200 mg, approximately 40:60 Form I:Form II) was dissolved in 0.3 ml of tetrahydrofuran at 50° C. Trifluorotoluene (1.5 ml) was added as an anti-solvent to cause precipitation. The resulting slurry was then cooled to 4° C. at 0.5° C./minute and stirred at 4° C. overnight to give pure Form I as the product.

(3S)-3-[N—(N'-(2-tert-Butylphenyl)oxamyl)alaninyl] amino-5-(2',3',5',6'-tetrafluorophenoxy)-4-oxopentanoic acid (200 mg, approximately 40:60 Form I:Form II) was dissolved in 0.8 ml of acetic acid at 50° C. n-Heptane (3.5 ml) was added as an anti-solvent to cause precipitation. The resulting slurry was then cooled to 4° C. at 0.5° C./minute and stirred at 4° C. overnight to give pure Form I as the product.

Preparation of Pure Form III from a Mixture of Forms I and II (3S)-3-[N—(N'-(2-tert-Butylphenyl)oxamyl)alaninyl] amino-5-(2',3',5',6'-tetrafluorophenoxy)-4-oxopentanoic acid (41 mg, approximately 75:25 Form I:Form II) was dissolved in methyl ethyl ketone (1 ml). The solution was filtered and allowed to evaporate slowly for 19 days, resulting in a gel. Toluene (10 μl) was added at this point. After another 3 days, an additional amount of toluene (100 μl) was added. After a further 4 days, a crystalline material corresponding to Form III was isolated.

Preparation of Pure Form III from Form I (3S)-3-[N—(N'-(2-tert-Butylphenyl)oxamyl)alaninyl]amino-5-(2',3',5',6'-tetrafluorophenoxy)-4-oxopentanoic acid (50 mg, Form I) was dissolved in methyl ethyl ketone (1 ml). The resulting clear solution was filtered, diluted with toluene (3 ml) and allowed to evaporate at ambient temperature for two days until an opaque material formed. The opaque solid was collected by vacuum filtration and air-dried under reduced pressure for approximately 10 minutes to yield 47.5 mg of Form III as the product.

In another experiment, (3S)-3-[N—(N'-(2-tert-Butylphenyl)oxamyl)alaninyl]amino-5-(2',3',5',6'-tetrafluorophenoxy)-4-oxopentanoic acid (700 mg, Form I) was dissolved in 14 ml of 2-butanone (methyl ethyl ketone) with sonication. The resulting clear solution was filtered into a beaker and diluted with toluene (42 ml). The solution was mixed well and allowed to evaporate at ambient temperature for 6 days until a gel-like opaque material formed. The gel-like material was vacuum filtered at room temperature for approximately 30 minutes to yield 633 mg of Form III. In another similar experiment the 2-butanone/toluene solution was allowed to evaporate at room temperature for 6 days. The solid produced was not vacuum filtered or further dried in air. The product was Form III (700 mg).

Preparation of Pure Form II by Dehydrogenation of a Benzyl Ester Precursor (with Seeding)

(3S)-3-[N—(N'-(2-tert-Butylphenyl)oxamyl)alaninyl]amino-5-(2',3',5',6'-tetrafluorophenoxy)-4-oxopentanoic acid benzyl ester (500 g, 0.758 mol) was added to tetrahydrofuran (2.5 litres), with stirring, at 20° C. Palladium on carbon (10%, 50 g) was then added and hydrogen was applied to the headspace above the liquid at 20 pounds per square inch (psi). After four hours, the catalyst was removed by filtration through a bed of Celite® and the filter cake was washed with tetrahydrofuran (2×1 litre). The filtrate was concentrated by evaporation at 30° C. under vacuum until a volume of 2 litres remained and n-heptane was then added, with stirring, over a period of an hour. A seed of form II (4.32 g) was added, and stirring continued for 3 hours at 20° C. Further n-heptane (2.35 litres) was then added and the suspension was stirred at 20° C. for 12 hours. The suspension was then cooled to −5° C. over six hours, stirred at this temperature for about one hour and filtered. The product was washed with n-heptane (2×1 litre) and oven-dried under vacuum at 40° C. for 16 hours to give pure form II (389 g).

As indicated above, the amorphous form of (3S)-3-[N—(N'-(2-tert-butylphenyl)oxamyl)alaninyl]amino-5-(2',3',5',6'-tetrafluorophenoxy)-4-oxopentanoic acid can be prepared by the specific and general processes described in patent application WO-A-00/01666. The compound may also be prepared by the route shown in Scheme 1 below. Naturally, the specific procedures employed in isolating the product may result in the preparation of the amorphous form or one of the crystalline forms of this invention.

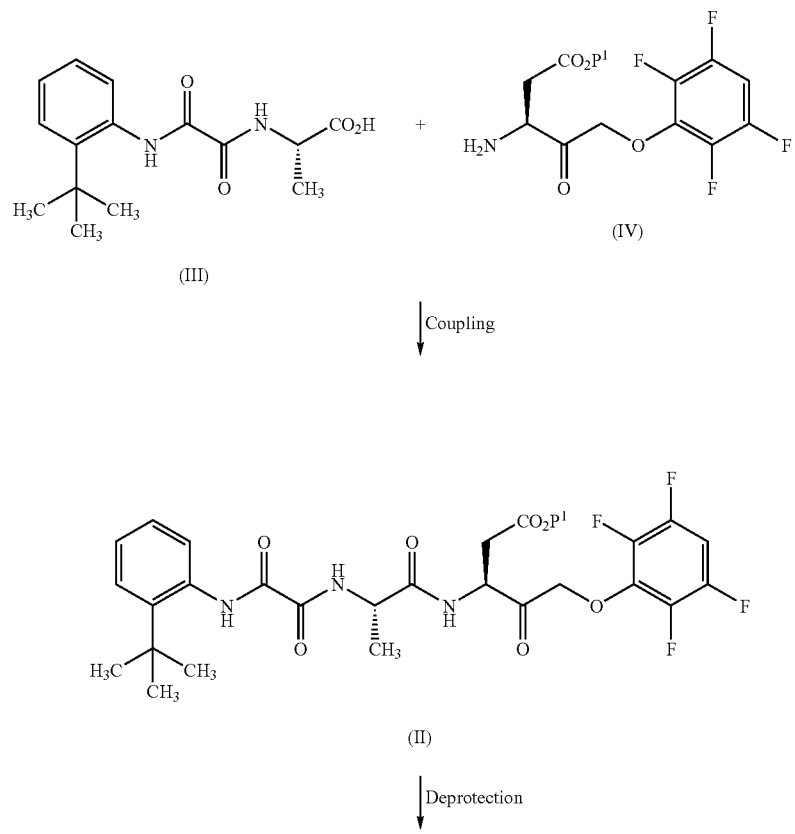

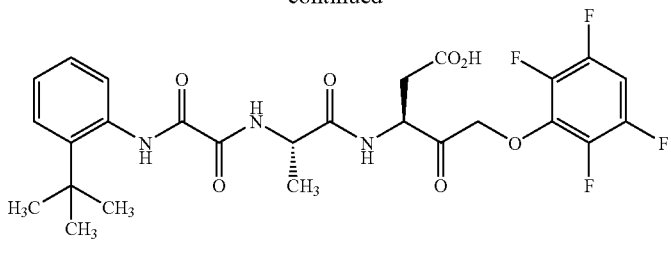

(I)

In Scheme 1, $P^1$ represents a suitable carboxyl protecting group, such as benzyl. Other examples of suitable protecting groups may be found in 'Protective Groups in Organic Synthesis' by Theorora Greene and Peter Wuts (third edition, 1999, John Wiley and Sons). A compound of formula (II) is therefore deprotected in order to provide the compound of formula (I), using conditions selected appropriately according to the choice of protecting group $P^1$. For instance, if $P^1$ is benzyl, a solution of the compound of formula (II) in a suitable solvent (such as tetrahydrofuran) may be treated with a hydrogenation catalyst (such as palladium on carbon) and exposed to an atmosphere of hydrogen gas. A compound of formula (II) may be prepared by coupling an acid of formula (III) with and an amine of formula (IV). The amine (IV) may optionally be used in the form of a salt such as the hydrochloride. Any suitable peptide coupling agents may be used. In a preferred process, a solution of amine (IV) and acid (III) in a suitable solvent (such as tetrahydrofuran) is treated with a chloroformate (such as isobutylchloroformate) and a base (such as N-methylmorpholine).

A compound of formula (III) can be prepared by the route shown in Scheme 2 below, wherein $R^x$ is a $C_1$-$C_6$ alkyl group, preferably methyl or ethyl.

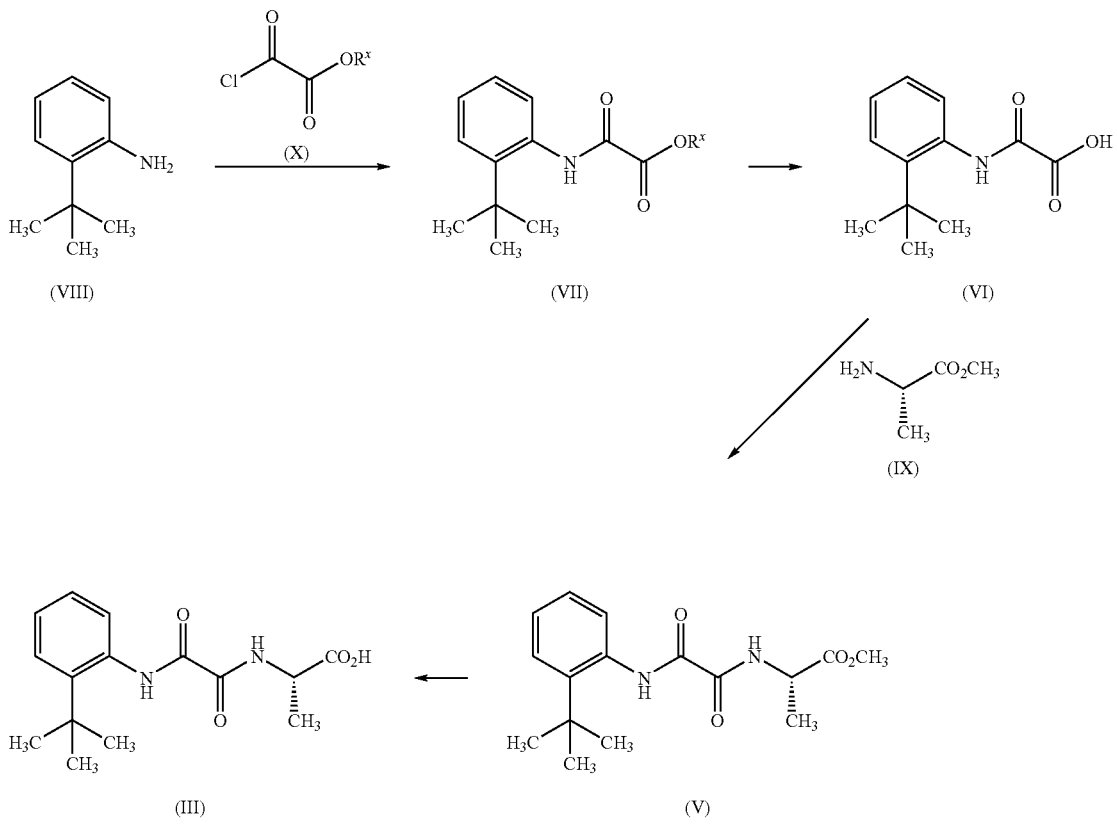

Scheme 2

The compound of formula (III) may be prepared by treating a compound of formula (V) with a suitable base in order to hydrolyse the ester functionality. In a preferred procedure, a solution of the compound of formula (V) in a suitable solvent (preferably tetrahydrofuran) is treated with an alkali metal hydroxide (preferably lithium hydroxide).

The compound of formula (V) may be prepared by coupling an acid of formula (VI) with an amine of formula (IX). The amine of formula (IX) may optionally be used as a salt, particularly as the hydrochloride salt. Any suitable peptide coupling agent may be used. In a preferred procedure, a solution of acid (VI) and amine (IX) in a suitable solvent (preferably dimethylformamide) is treated with a carbodiimide coupling agent in the presence of a base such as N-methylmorpholine.

The compound of formula (VI) may be prepared by treating a compound of formula (VII) with a base in order to hydrolyse the ester functionality. In a preferred procedure, a solution of the compound of formula (VI) in a suitable solvent (preferably toluene) is treated with an alkali metal hydroxide (preferably sodium hydroxide).

A compound of formula (VII) may be prepared by treating an amine of formula (VIII) with a compound of formula (X) in the presence of an amine base. In a preferred procedure, a solution of compounds (VIII) and (X) in a suitable solvent (preferably toluene) are treated with triethylamine.

A compound of formula (IV) (see Scheme 1) may be prepared by the route shown in Scheme 3 below, wherein $P^1$ is as defined above and $P^2$ is a suitable amine protecting group (preferably a tert-butyloxycarbonyl group, BOC). Examples of suitable amine protecting groups may be found in 'Protective Groups in Organic Synthesis' by Theorora Greene and Peter Wuts (third edition, 1999, John Wiley and Sons).

The compound of formula (IV) may be prepared by deprotecting a compound of formula (XI), using conditions selected appropriately according to the choice of protecting group $P^2$. For instance, if $P^1$ is tert-butyloxycarbonyl then a solution of the compound of formula (XI) in a suitable solvent (preferably ethyl acetate) is treated with an acid (preferably hydrochloric acid). Care must be taken in the choice of protecting groups $P^1$ and $P^2$ so that the conditions necessary to remove protecting group $P^2$ do not also remove protecting group $P^1$.

A compound of formula (XI) may be prepared by displacing the bromide group in a compound of formula (XII) with the phenolate anion derived by deprotonation of 2,3,5,6-tetrafluorophenol. Preferably an alkali metal salt of the phenol is used, most preferably the potassium salt. Suitable deprotonating agents are therefore sodium or potassium hydride. In a preferred procedure, a solution of the compound of formula (XII) in a suitable solvent (preferably acetone) is treated with the deprotonated phenol in the presence of a nucleophilic catalyst (preferably sodium iodide).

A compound of formula (XII) may be prepared by diazomethane mediated homologation of an acid of formula (XIII). In a typical procedure, a solution of the compound of formula (XIII) in a suitable solvent (preferably tetrahydrofuran) is treated successively with (a) a chloroformate (preferably isobutylchloroformate) and a base (preferably N-methylmorpholine), (b) diazomethane and (c) hydrogen bromide.

Compounds used in the foregoing procedures whose preparation has not be described, such as compounds of formula (VIII), (IX), (X) and (XIII) are commercially available and/or can be prepared by routine procedures within the skilled person's common general knowledge.

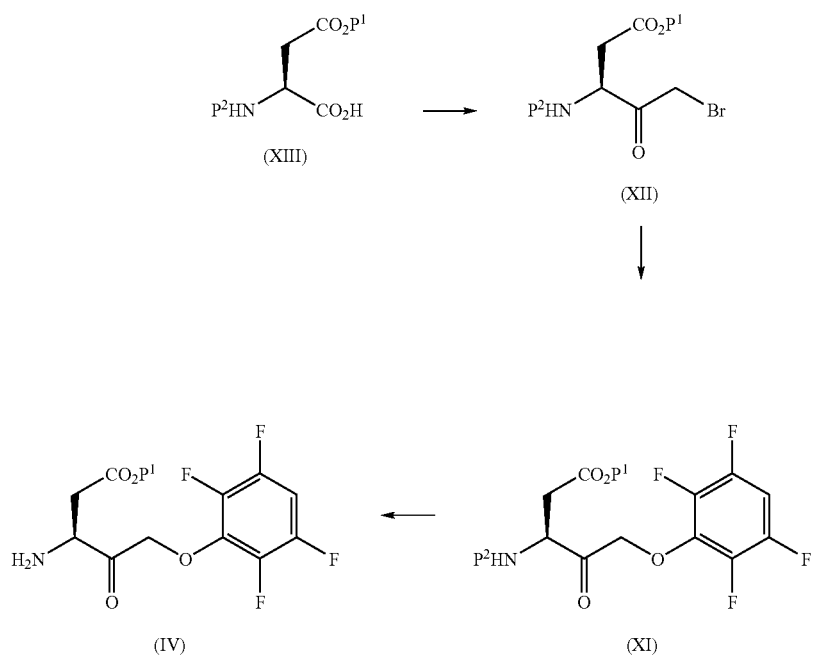

A compound of formula (XII) may also be prepared by treating a compound of formula:

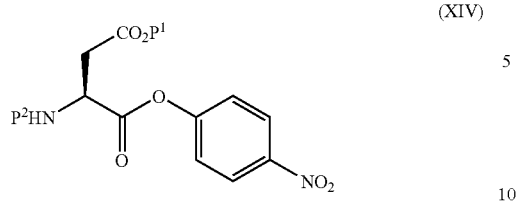

(XIV)

wherein $P^1$ and $P^2$ are as defined above, with trimethylsulphonium oxide $((CH_3)_3S=O)$ in the presence of a base and subsequent addition of a source of bromide (e.g. hydrogen bromide or lithium bromide).

A compound of formula (V) may also be conveniently prepared in a one-pot procedure by sequentially treating a compound of formula:

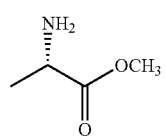

(XV)

or an acid salt thereof (particularly the hydrochloride salt) firstly with oxalyl chloride (ClCOCOCl) and secondly with 2-tert-butylaniline.

A compound of formula (XI) may alternatively be prepared by the route shown in Scheme 4 below. $P^1$ and $P^2$ are protecting groups as defined above. In a preferred embodiment, $P^1$ is benzyl and $P^2$ is tert-butyloxycarbonyl.

Scheme 4

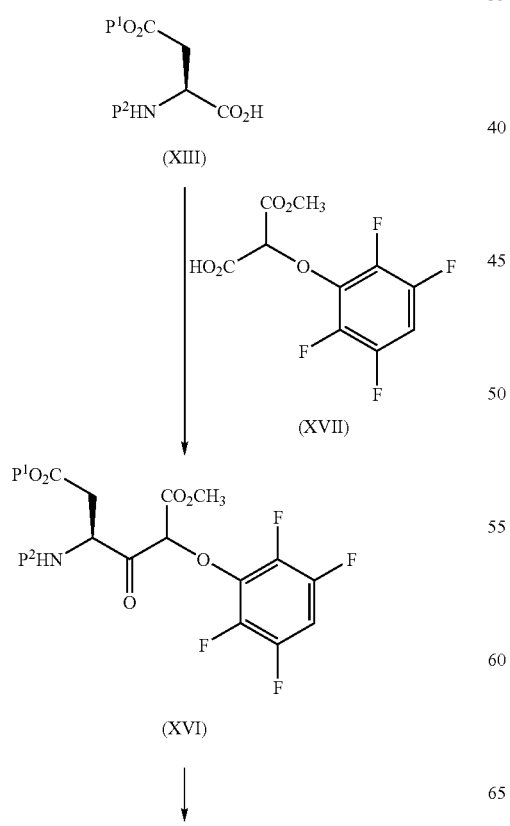

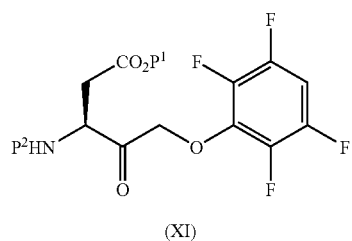

(XI)

A compound of formula (XI) may thus be prepared by selective hydrolysis and decarboxylation of a compound of formula (XVI). Care must be taken to ensure that the methyl ester moiety of compound (XVI) is more reactive and therefore more easily hydrolysed than the protected carbonyl group —$CO_2P^1$, especially where the latter group is also an ester. A typical hydrolysing agent is sodium hydroxide.

A compound of formula (XVI) may be prepared by activating a compound of formula (XIII) and treating the activated species with a doubly deprotonated form of a compound of formula (XVII). Nucleophilic addition occurs followed by decarboxylation. Activation may be achieved by treating a compound of formula (XIII) with an amide coupling agent such as a carbodiimide.

A compound of formula (XVII) may be prepared by treating □-chloro-dimethylmalonate with a deprotonated form of 2,3,5,6-tetrafluorobenzene and selectively hydrolysing one of the methyl ester groups in the product.

A compound of formula (XI) may also be prepared by the route shown in Scheme 5. $P^1$ and $P^2$ are protecting groups as defined above. In a preferred embodiment, $P^1$ is benzyl and $P^2$ is tert-butyloxycarbonyl.

Scheme 5

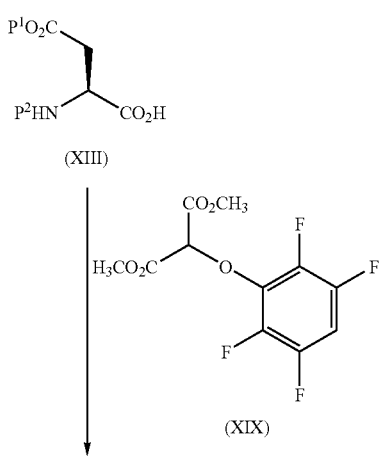

-continued

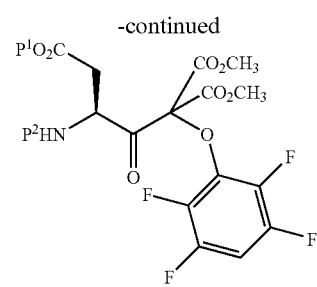

(XVIII)

↓

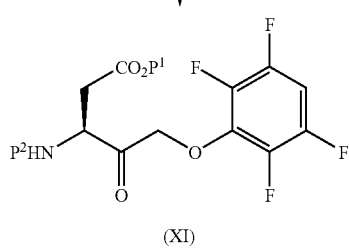

(XI)

A compound of formula (XI) may thus be prepared by the selective double hydrolysis and decarboxylation of a compound of formula (XVIII). Care must be taken to ensure that the methyl ester moieties of compound (XVIII) are more reactive and therefore more easily hydrolysed than the protected carbonyl group —CO$_2$P$^1$, especially where the latter group is also an ester. A typical hydrolysing agent is sodium hydroxide.

A compound of formula (XVIII) may be prepared by activating a compound of formula (XIII) and treating the activated species with a deprotonated form of a compound of formula (XIX). Activation may be achieved by treating a compound of formula (XIII) with an amide coupling agent such as a carbodiimide.

A compound of formula (XIX) may be prepared by treating ☐-chloro-dimethylmalonate with a deprotonated form of 2,3,5,6-tetrafluorobenzene.

A compound of formula (XI) may also be prepared by activating a compound of formula (XIII) (wherein P$^1$ and P$^2$ are protecting groups, as defined above, preferably benzyl and tert-butyloxycarbonyl respectively) and treating this activated species with a doubly deprotonated form of a compound of formula:

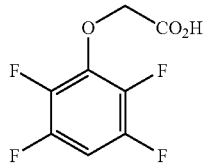

(XX)

Activation may be achieved by treating a compound of formula (XIII) with an amide coupling agent such as a carbodiimide.

A compound of formula (XX) may be prepared by treating an acetic acid derivative with a leaving group at the 2-position (e.g. 2-chloroacetic acid) with a deprotonated form of 2,3,5,6-tetrafluorophenol.

A compound of formula (XI) may also be prepared as shown in Scheme 6. P$^1$ and P$^2$ are protecting groups as defined above. In a preferred embodiment, P$^1$ is benzyl and P$^2$ is tert-butyloxycarbonyl.

Scheme 6

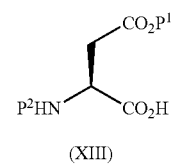

(XIII)

↓

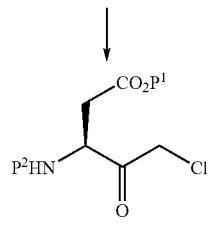

(XXI)

↓

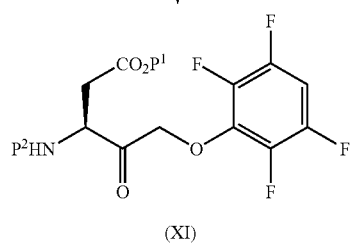

(XI)

A compound of formula (XI) may be prepared by displacing the chloro group in a compound of formula (XXI) with the phenolate anion derived by deprotonation of 2,3,5,6-tetrafluorophenol. Preferably an alkali metal salt of the phenol is used, most preferably the potassium salt. Suitable deprotonating agents are therefore sodium or potassium hydride. In a preferred procedure, a solution of the compound of formula (XXI) in a suitable solvent (preferably acetone) is treated with the deprotonated phenol in the presence of a nucleophilic catalyst (preferably sodium iodide).

A compound of formula (XXI) may be prepared by activating a compound of formula (XIII) and treating the activated species with a doubly deprotonated form of 2-chloroacetic acid. Activation may be achieved by conversion to an ester or by treatment with an amide coupling agent such as a carbodiimide. In a preferred procedure, a solution of sodium chloroacetate in a suitable solvent (such as tetrahydrofuran) is treated with zinc chloride and diisopropylaminomagnesium chloride and then added to a solution of the methyl ester of a compound of formula (XIII).

A drug substance must be suitable for formulation in a dosage form chosen according to the intended route of administration. The most popular kind of pharmaceutical formulation is a tablet or capsule, such a dosage form being easily and conveniently administered via the oral route. For formulation as a tablet or capsule, a drug substance should be non-hygroscopic and compressible. Hygroscopicity can lead to problems with processing and a short shelf life—potency of material can change during processing steps due to the uptake of water and water uptake can lead to poor flow characteristics (i.e. sticking). A suitable drug substance should also possess a solubility and rate of dissolution that leads to rapid bioavailability on exposure to the gastric environment. The crystalline forms of (3S)-3-[N—(N'-(2-tert-butylphenyl)oxamyl)alaninyl]amino-5-(2',3',5',6'-tetrafluorophenoxy)-4-oxopentanoic acid described above have excellent properties of this kind and are suitable for formulation in tablets and capsules. Form II is particularly suitable.

Hygroscopicity was assessed for forms I and II using dynamic vapour sorption (DVS). The samples were characterised using a Surface Measurement Systems Ltd, dynamic vapour sorption equipment, model DVS-1. The analysis was conducted at 30° C. with a nitrogen gas flow of 200 cc/min. Water sorption and desorption were determined in the range 0 to 90% relative humidity (RH) using 15% RH intervals. Exposure was for a minimum of two hours at each humidity, or until the rate of weight change was less than 0.0005%/minute (averaged over 10 minutes). Sample weights were in the range 23-36 mg. The samples were weighed using a CAHN D-200, seven place digital recording balance, which is an integral part of the equipment. The results are tabulated below in Tables 6 and 7 and plotted in FIGS. 15 and 16.

TABLE 6

Water sorption data for Form I

| % RH | Water Sorption (% w/dry w) | |
|---|---|---|
| | Sorption | Desorption |
| 15 | 0.018 | 0.015 |
| 30 | 0.028 | 0.025 |
| 45 | 0.049 | 0.037 |
| 60 | 0.072 | 0.055 |
| 75 | 0.110 | 0.105 |
| 90 | 0.208 | 0.208 |

TABLE 7

Water sorption data for Form II

| % RH | Water Sorption (% w/dry w) | |
|---|---|---|
| | Sorption | Desorption |
| 15 | 0.007 | 0.009 |
| 30 | 0.014 | 0.015 |
| 45 | 0.020 | 0.021 |
| 60 | 0.029 | 0.031 |
| 75 | 0.042 | 0.044 |
| 90 | 0.057 | 0.057 |

The present invention includes all pharmaceutically acceptable isotopically-labelled variants of the crystalline forms provided by the present invention. In an isotopically-labelled variant, one or more atoms are replaced by an atom or atoms having the same atomic number, but an atomic mass or mass number different from the atomic mass or mass number which predominates in nature.

Suitable isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; and sulphur, such as $^{35}$S.

Certain isotopically-labelled compounds, such as those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds can be prepared by conventional techniques known to those skilled in the art using an appropriate isotopically-labeled reagent in place of the non-labeled reagent previously employed.

(3S)-3-[N—(N'-(2-tert-Butylphenyl)oxamyl)alaninyl]amino-5-(2',3',5',6'-tetrafluorophenoxy)-4-oxopentanoic acid is an irreversible pan-caspase inhibitor which inhibits cellular apoptosis, as described in WO-A-00/01666, and the crystalline forms of the compound provided by the present invention are therefore potentially useful in the treatment of a range of conditions including infectious diseases (e.g. meningitis, salpingitis), septic shock, respiratory diseases, inflammatory conditions (e.g. arthritis, cholangitis, colitis, encephalitis, hepatitis, biliary atresia, lens scarring, pancreatitis, reperfusion injury), ischemic diseases (e.g. myocardial infarction, stroke, ischemic kidney disease), immune-based diseases (e.g. hypersensitivity), auto-immune diseases (e.g. multiple sclerosis), bone diseases, type II diabetes (through the reduction of insulin resistance) and neurodegenerative diseases (e.g. Alzheimer's disease, Parkinson's disease). They are also potentially useful for the repopulation of hematopoietic cells following chemotherapy or radiation therapy and for prolonging organ viability for use in transplantation (particularly the liver). Caspase inhibitors can further be used to expand or increase the survival of a cell population in vitro and hence have application in increasing the efficiency of bioproduction.

The crystalline forms of the present invention are particularly useful in the treatment and prevention of liver fibrosis. Liver fibrosis is a result of the body's attempt to deal with various forms of hepatitis (liver inflammation) and leads to liver impairment, cirrhosis and eventually death. The fibrosis (scarring) is caused by the deposition of collagen, leading to reduced liver function, and eventually to cirrhosis. If the cirrhotic liver is not transplanted then death may result. The hepatitis from which fibrosis results may be caused by a range of different insults to the liver, including viral infections (particularly hepatitis B and hepatitis C), the deposition of too much fat (non-alcoholic steatohepatitis (NASH)) and alcohol.

The crystalline forms of (3S)-3-[N—(N'-(2-tert-butylphenyl)oxamyl)alaninyl]amino-5-(2',3',5',6'-tetrafluorophenoxy)-4-oxopentanoic acid provided by the present invention (henceforth referred to as the compounds of the invention) may be administered alone but will generally be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Pharmaceutical compositions suitable for the delivery of the compounds of the invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the compounds of the invention may make up from 1 weight % to 80 weight % of the dosage form, more typically from 5 weight % to 60 weight % of the dosage form.

In addition, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are also generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible tablet ingredients include anti-oxidants, colouring agents, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller compaction to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

The compounds of the invention may also be orally administered in the form of a consumable oral film for human or veterinary use. Such a film is typically a pliable water-soluble or water-swellable thin film dosage form which may be rapidly dissolving or mucoadhesive and typically comprises the compound of the invention, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible film ingredients include anti-oxidants, colouring agents, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuum drying.

Solid formulations for oral administration may be formulated to be immediate and/or modified release delayed, sustained, pulsed, controlled, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO-A-00/35298.

The compounds of the invention may also be administered directly into the blood stream, into muscle, or into an internal organ. Such parenteral administration may be via the intravenous, intraarterial, intraperitoneal, intrathecal, intraventricular, intraurethral, intrasternal, intracranial, intramuscular or subcutaneous route. Suitable devices for parenteral administration include needle (including microneedle) injectors, needle-free injectors and infusion techniques.

Parenteral formulations are typically aqueous solutions which may contain excipients such as salts, carbohydrates and buffering agents (a pH of from 3 to 9 is preferred), but, for some applications, they may be more suitably formulated as a sterile non-aqueous solution or as, dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations for parenteral administration may be formulated to be immediate and/or modified release. Modified release includes delayed, sustained, pulsed, controlled, targeted and programmed release. Thus compounds of the invention may be formulated as a solid, semi-solid or thixotropic liquid for administration as an implanted depot providing modified release of the compound of the invention. Examples of such formulations include drug-coated stents and poly(dl-lactic-coglycolic)acid (PGLA) microspheres.

The compounds of the invention may also be administered topically to the skin or mucosa, i.e. dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958, Finnin and Morgan (October 1999). Other means of topical administration include delivery by electroporation, iontophoresis, phonophoresis, sonophoresis and microneedle or needle-free (e.g. Powderject™, Bioject™) injection.

Formulations for topical administration may be formulated to be immediate and/or modified release. Modified release includes delayed, sustained, pulsed, controlled, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer or nebuliser contains a solution or suspension of the compound of the invention comprising, for example, ethanol, aqueous ethanol or a suitable alternative agent for dispersing, solubilising or extending release of the active, a propellant(s) as solvent and an optional surfactant, such as sorbitan trioleate, oleic acid or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of the invention, propylene glycol, sterile water, ethanol and sodium chloride. Alternative solvents which may be used instead of propylene glycol include glycerol and polyethylene glycol.

Suitable flavouring agents, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release includes delayed, sustained, pulsed, controlled, targeted and programmed release.

In the case of dry powder inhalers and aerosols, the dosage unit is determined by means of a valve which delivers a metered amount. The overall daily dose may be administered in a single dose or, more usually, as divided doses throughout the day.

The compounds of the invention may be administered rectally or vaginally, in the form, for example, of a suppository, pessary or enema. Cocoa butter is a traditional suppository base, but various alternatives may be used as appropriate.

Formulations for rectal/vaginal administration may be formulated to be immediate and/or modified release. Modified release includes delayed, sustained, pulsed, controlled, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose or methyl cellulose or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release includes delayed, sustained, pulsed, controlled, targeted, and programmed release.

The compounds of the invention may be combined with a soluble macromolecular entity, such as a cyclodextrin or a suitable derivative thereof or a polyethylene glycol-containing polymer, in order to improve solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in WO-A-91/11172, WO-A-94/02518 and WO-A-98/55148.

For administration to human patients, the total daily dose of the compound of the invention will typically be in the range 0.01 mg/kg to 100 mg/kg depending, of course, on the mode of administration. The total daily dose per subject via the oral route will typically be in the range 1 to 100 mg. The total daily dose may be administered as a single dose or as divided doses and may, at the physician's discretion, fall outside of the typical ranges given herein.

For the avoidance of doubt, references herein to "treatment" include references to curative, palliative and prophylactic treatment.

A pan-caspase inhibitor (particularly (3S)-3-[N—(N'-(2-tert-butylphenyl)oxamyl)alaninyl]amino-5-(2',3',5',6'-tetrafluorophenoxy)-4-oxopentanoic acid, most particularly one of the crystalline forms of the present invention) may be usefully combined with another pharmacologically active compound, or with two or more other pharmacologically active compounds, particularly in the treatment of liver fibrosis. For example, such an inhibitor may be administered simultaneously, sequentially or separately in combination with one or more agents selected from:

an antiviral agent such as ribaviron or interferon;
a CCR-5 antagonist;
an insulin sensitiser such as metformin;
a hepatoprotectant such as vitamin E, pentoxiphylline, betaine or ursodeoxycholic acid;
a lipid-lowering agent such as accomplia, orlistat, fibrates or cholestyramine;
an HMG-CoA reductase inhibitor such as atorvastatin;
a glitasone;
a biological agent such as an anti-TNF☐ antibody or an anti-MAdCAM antibody; and
an immunosuppressant such as cyclosporine or tacrolimus;

and, where appropriate, the pharmaceutically acceptable salts and solvates thereof.

Inasmuch as it may desirable to administer a combination of active compounds, it is within the scope of the present invention that two or more pharmaceutical compositions, at least one of which contains the compound of the invention, may conveniently be combined in the form of a kit suitable for co-administration of the compositions.

Such a kit comprises two or more separate pharmaceutical compositions, at least one of which contains the compound of the invention, and means for separately retaining said compositions, such as a container, divided bottle, or divided foil packet. An example of such a kit is the familiar blister pack used for the packaging of tablets, capsules and the like.

Such a kit is particularly suitable for administering different dosage forms, for example, oral and parenteral dosage forms, for administering the separate compositions at different dosage intervals, or for titrating the separate compositions against one another. To assist compliance, the kit typically comprises directions for administration and may be provided with a so-called memory aid.

The invention claimed is:

1. A crystalline form I of (3S)-3-[N—(N'-(2-tert-butylphenyl)oxamyl)alaninyl]amino-5-(2', 3',5', 6'-tetrafluorophenoxy)-4-oxopentanoic acid having unique peaks at 7.7, 14.1, 21.4, 26.6 and 29.4 degrees two theta (±0.1 degrees) when analysed by powder X-ray diffraction using copper K-alpha$_1$ radiation (wavelength=1.5406 Angstroms).

2. A crystalline form II of (3S)-3-[N—(N'-(2-tert-butylphenyl)oxamyl)alaninyl]amino-5-(2', 3', 5', 6'-tetrafluorophenoxy)-4-oxopentanoic acid having unique peaks at 14.5 17.3, 22.5, 25.0 and 26.8 degrees two theta (±0.1 degrees) when analysed by powder X-ray diffraction using copper K-alpha$_1$ radiation (wavelength=1.5406 Angstroms).

3. A crystalline form III of (3S)-3-[N—(N'-(2-tert-butylphenyl)oxamyl)alaninyl]amino-5-(2', 3', 5', 6'-tetrafluorophenoxy)-4-oxopentanoic acid having unique peaks at 7.2 8.1, 8.4, 12.4 and 38.5 degrees two theta (±0.1 degrees) when analysed by powder X-ray diffraction using copper K-alpha$_1$ radiation (wavelength=1.5406 Angstroms).

4. A pharmaceutical solid composition comprising a crystalline form according to any one of claims 1 to 3 and a pharmaceutically acceptable excipient.

5. A method of treating liver fibrosis in a mammal comprising administering to said mammal an effective amount of a crystalline form according to any one of claims 1 to 3.

6. The pharmaceutical solid composition of claim 5 further comprising a second pharmacologically active substance.

\* \* \* \* \*